US006235521B1

(12) United States Patent
Nakanishi et al.

(10) Patent No.: US 6,235,521 B1
(45) Date of Patent: May 22, 2001

(54) PHAGE BONDED TO A NUCLEAR LOCATION SIGNAL

(75) Inventors: Mahito Nakanishi; Emi Nagoshi, both of Osaka; Teruo Akuta, Ibaraki; Katsuo Takeda, Ibaraki; Mamoru Hasegawa, Ibaraki, all of (JP)

(73) Assignee: Dnavec Research, Ibaraki (JP)

( * ) Notice: Subject to any disclaimer, the term of this patent is extended or adjusted under 35 U.S.C. 154(b) by 0 days.

(21) Appl. No.: 09/242,131
(22) PCT Filed: Dec. 27, 1996
(86) PCT No.: PCT/JP96/03861
  § 371 Date: Sep. 10, 1999
  § 102(e) Date: Sep. 10, 1999
(87) PCT Pub. No.: WO98/06828
  PCT Pub. Date: Feb. 19, 1998

(30) Foreign Application Priority Data

Aug. 9, 1996 (JP) .................................................. 8-227787

(51) Int. Cl.[7] .............................. C12N 7/00; C12N 15/09; C12N 15/86; A01N 63/00
(52) U.S. Cl. .................... 435/320.1; 424/93.6; 424/93.2; 435/456
(58) Field of Search .............................. 435/320.1, 456; 424/93.2, 93.6

(56) References Cited

U.S. PATENT DOCUMENTS 5,627,024  5/1997  Maruyama et al. ..................... 435/5

OTHER PUBLICATIONS

Oldenburg, et al. Proceedings of the National Academy of Sciences, USA vol. 89 pp. 5393–5397, Jun. 1992.*
Greber et al., "Nuclear targeting of SV40 and adenovirus," *Trends in Cell Biology* 6:189–195 (1996).
Maruyama et al., "λfoo: A λ phage vector for the expression of foreign proteins," *Proc. Natl. Acad. Sci. USA* 91:8273–8277 (1994).
Mikawa et al., "Surface display of proteins on bacteriophage λ heads," *J. Mol. Biol.* 262(1):21–30 (1996).
Sternberg et al., "Display of peptides and proteins on the surface of bacteriophage λ," *Proc. Natl. Acad. Sci. USA* 92(5):1609–1613 (1995).
Zabner et al., "Cellular and molecular barriers to gene transfer by a cationic lipid," *J. Biol. Chem.* 270(32): 18997–19007 (1995).

* cited by examiner

Primary Examiner—David Guzo
Assistant Examiner—Gerald G. Leffers, Jr.
(74) Attorney, Agent, or Firm—Clark & Elbing LLP

(57) ABSTRACT

A λ phage with a nuclear localization signal has been obtained by constructing a vector capable of expressing a fused protein between a gpD protein constituting the head of a λ phage and a nuclear localization signal sequence, transforming *Escherichia coli* with this vector, and propagating a mutant λ phage which cannot express the gpD protein in *E. coli* in this transformant. It has been confirmed that the resulting λ phage is capable of packaging λ phage DNAs of 80% and 100% genome sizes. After further confirming that the nuclear localization signal exposed on the outside of the head of this phage, this phage has been microinjected into cells to analyze its nuclear localization activity. Thus, it has been clarified that this phage has a nuclear localization activity.

6 Claims, 3 Drawing Sheets gpD

SV40VP1NLS                         MKMAPTKRKGSAPGAAPKKPKT

SV40 large T antigen NLS           MYDDEATADSQHSTPPKKKRKVEDPKDFESELLST

Hepatitis D virus δ antigen NLS    MKKDKDGEGAPPAKKLRMDQMEIDAGPRKRPT

Angiotensin II 8 peptide           MS<u>DRVYIHPF</u> [GAPSVGRT] 
                                              ↑
                                        Spacer protein
                                              ↓
SV40 large T antigen minimum NLS   M<u>PKKKRKV</u> [GAPSVGRT]

SV40 large T antigen minimum NLS   M<u>PKKKRKV</u>T

λ phage with the nuclear localization signal

λ phage with the nuclear localization signal

Unmodified λ phage

Unmodified λ phage

Wild type λ phage

λ phage with the nuclear localization signal

SEQUENCE LISTING

<160> NUMBER OF SEQ ID NOS: 12

<210> SEQ ID NO 1
<211> LENGTH: 20
<212> TYPE: PRT
<213> ORGANISM: Simian virus 40

<400> SEQUENCE: 1

Lys Met Ala Pro Thr Lys Arg Lys Gly Ser Ala Pro Gly Ala Ala Pro
1               5                   10                  15

Lys Lys Pro Lys
            20

<210> SEQ ID NO 2
<211> LENGTH: 33
<212> TYPE: PRT
<213> ORGANISM: Simian virus 40

<400> SEQUENCE: 2

Tyr Asp Asp Glu Ala Thr Ala Asp Ser Gln His Ser Thr Pro Pro Lys
1               5                   10                  15

Lys Lys Arg Lys Val Glu Asp Pro Lys Asp Phe Glu Ser Glu Leu Leu
            20                  25                  30

Ser

<210> SEQ ID NO 3
<211> LENGTH: 30
<212> TYPE: PRT
<213> ORGANISM: Hepatitis D virus

<400> SEQUENCE: 3

Lys Lys Asp Lys Asp Gly Glu Gly Ala Pro Pro Ala Lys Lys Leu Arg
1               5                   10                  15

Met Asp Gln Met Glu Ile Asp Ala Gly Pro Arg Lys Arg Pro
            20                  25                  30

<210> SEQ ID NO 4
<211> LENGTH: 7
<212> TYPE: PRT
<213> ORGANISM: Simian virus 40

<400> SEQUENCE: 4

Pro Lys Lys Lys Arg Lys Val
1               5

```
<210> SEQ ID NO 5
<211> LENGTH: 26
<212> TYPE: DNA
<213> ORGANISM: Bacteriophage lambda

<400> SEQUENCE: 5
gtaagccatg gttatgacga gcaaag                                        26

<210> SEQ ID NO 6
<211> LENGTH: 32
<212> TYPE: DNA
<213> ORGANISM: Bacteriophage lambda

<400> SEQUENCE: 6
gttcgaattc ctattaaacg atgctgattg cc                                 32

<210> SEQ ID NO 7
<211> LENGTH: 22
<212> TYPE: PRT
<213> ORGANISM: Homo sapiens

<400> SEQUENCE: 7
```

Met Lys Met Ala Pro Thr Lys Arg Lys Gly Ser Ala Pro Gly Ala Ala
 1               5                  10                  15

Pro Lys Lys Pro Lys Thr
                20

```
<210> SEQ ID NO 8
<211> LENGTH: 35
<212> TYPE: PRT
<213> ORGANISM: Simion Virus 40

<400> SEQUENCE: 8
```

Met Tyr Asp Asp Glu Ala Thr Ala Asp Ser Gln His Ser Thr Pro Pro
 1               5                  10                  15

Lys Lys Lys Arg Lys Val Glu Asp Pro Lys Asp Phe Glu Ser Glu Leu
                20                  25                  30

Leu Ser Thr
        35

```
<210> SEQ ID NO 9
<211> LENGTH: 32
<212> TYPE: PRT
<213> ORGANISM: Simion Virus 40

<400> SEQUENCE: 9
```

Met Lys Lys Asp Lys Asp Gly Glu Gly Ala Pro Pro Ala Lys Lys Leu
 1               5                  10                  15

Arg Met Asp Gln Met Glu Ile Asp Ala Gly Pro Arg Lys Arg Pro Thr
                20                  25                  30

```
<210> SEQ ID NO 10
<211> LENGTH: 18
<212> TYPE: PRT
<213> ORGANISM: Homo sapiens

<400> SEQUENCE: 10
```

Met Ser Asp Arg Val Tyr Leu His Pro Phe Gly Ala Pro Ser Val Gly
 1               5                  10                  15

Arg Thr

```
<210> SEQ ID NO 11
```

```
<211> LENGTH: 16
<212> TYPE: PRT
<213> ORGANISM: Simion Virus 40

<400> SEQUENCE: 11

Met Pro Lys Lys Lys Arg Lys Val Gly Ala Pro Ser Val Gly Arg Thr
 1               5                  10                  15

<210> SEQ ID NO 12
<211> LENGTH: 9
<212> TYPE: PRT
<213> ORGANISM: Simion Virus 40

<400> SEQUENCE: 12

Met Pro Lys Lys Lys Arg Lys Val Thr
 1               5
```

PHAGE BONDED TO A NUCLEAR LOCATION SIGNAL

TECHNICAL FIELD

The present invention relates to the field of genetic engineering, especially to the transportation of exogenous materials by means of virus particles.

BACKGROUND ART

The gene transfer technology to artificially introduce an exogenous gene into cells is an important technology not only as a fundamental technology to analyze a variety of biological phenomena but also as one which leads to useful applications such as gene therapy and production of beneficial animals. Generally, two methods have been used for gene transfer. One is a biological method using a virus having an exogenous gene, and the other is a physical method in which an exogenous gene is physically introduced into cells.

The method using a virus is based on the principle that a cell is infected with a recombinant virus in which the gene of interest is incorporated, and the entire recombinant virus genome integrates into the genome of the host cell. This method is currently attracting much attention as a technological basis for gene therapy for such diseases as Lesch-Nyhan syndrome and adenosine deaminase (ADA) deficiency. However, it has been pointed out that the method has various problems such as the pathogenicity of the virus since it utilizes the biological properties of the virus itself. For this reason, modified retroviral vectors without the regions associated with the viral pathogenicity and replication have currently being developed. However, these modified vectors have yet many problems that they might still cause some undesirable effects on cells, and they can infect only dividing cells.

Therefore, physical methods to introduce non-viral vectors are now used as well as the above-mentioned methods using viruses. In one of the established physical methods, non-viral vectors are introduced into cells in combination with chemicals such as calcium phosphate., DEAE-dextran, polycations, or liposomes. However, these physical methods have such problems that the transfection efficiency of genes into cells is low, and that the exogenous gene on a non-viral vector thus transfected does not reach the cell nucleus in many cases. Therefore, the methods have many difficulties to be overcome for being applied to gene therapy.

Recently, it was reported that the proteins which are transported into the nucleus of eukaryotic cells and function there have a specific amino acid sequence that functions as a signal (NLS: nuclear localization signal) for their transportation into the nucleus (G. Garcia-Bustos et al., Biochem. Biophys. Acta 1071: 83–101 (1991)). Moreover, it was also reported that attaching the nuclear localization signal to a protein that normally does not translocate to the nucleus will confer the nuclear translocation activity on this protein (R. E. Lanford et al., Cell 46: 575–582 (1986), Y. Yoneda et al., Exp. Cell. Res. 170: 439–452 (1987), D. Chelsky et al., Mol. Cell. Biol. 9: 2487–2492 (1989)). Based on this knowledge, researches have been made using the nuclear localization signal so that the gene introduced by physical methods can reach the nucleus with a high probability. That is, the techniques are studied to condense DNA as close as possible to 40 nm, the size of the nuclear membrane pore, attach the nuclear localization signal to this condensate, and thereby actively transport the DNA to the nucleus. For example, efforts have been made to make DNA more compact by using proteins such as HMG-1 and histones, as well as poly-L-lysines (Jose C. Perales et al., E. J. B. 266: 255–266 (1994)), and cationic liposomes (J. Zabner et al., J. B. C. 270: 18997–19007 (1995)).

However, the synthetic chemical approach had problems with solubility and homogeneity of the complex with DNA, and with the varying degrees of condensation of DNA dependent on the salt concentration. Moreover, construction of the complex is possible only under highly alkaline conditions and impossible under physiological conditions, which has been one of the problems to be solved for practical use.

It has been suggested that, on the viruses that infect animals such as adenovirus and SV40, the nuclear localization signals exist in their capsid proteins, and they function to actively translocate their DNA at the early stage of infection (Urs. F. Greber and Harumi Kasamatsu, Trends in Cell Biology 6: 189–195 (1996)). It has been also suggested that the SV40 particle with its diameter of 45 nm invade the nucleus in the form of virion (K. Hummeler et al., J. Virol. 6: 87–93 (1970)). Furthermore, MS-2 phage is reported to have a transport system in which exogenous substances are enveloped by the capsid (International Application published in Japan No. Hei-508168). However, any transport system using virus particles, which is capable of using long chain DNA and translocating the DNA into the nucleus, has not been reported.

DISCLOSURE OF THE INVENTION

An objective of the present invention is to provide a system that enables delivering genes introduced into cells to the nucleus. More specifically, the objective of the invention is to provide a λ phage with a nuclear localization signal exposed on the outer surface of its head, and capable of packaging long chain DNA.

In order to translocate long chain DNA into the nucleus, it is necessary to condense the DNA to nearly 40 nm, the size of nuclear membrane pore. The present inventors paid attention to the head of a λ phage, which is able to compactly package desired long chain DNA in vitro and to protect the DNA from the attack by external DNases, and used it as a carrier of the DNA. Furthermore, we paid attention to the phenomena that the viruses that infect animals can invade the nucleus in the form of virion in virtue of nuclear localization signals in their capsid proteins, and attempted to actively transport DNA into the nucleus by preparing and using the λ phage head to which a nuclear localization signal has been attached. More specifically, we used the following steps.

First, we constructed a vector that expresses a fusion protein between the gpD protein, which is one of the proteins to constitute the λ phage head, and the nuclear localization signal sequence, transformed *Escherichia coli* with this vector, then infected the transformants with a mutant λ phage incapable of expressing gpD in the *E. coli* cells (hereinafter designated as "D amber phage"). By plaque formation analysis and western blot analysis using an anti-gpD antibody, we have confirmed that the mutant phage was complemented by the fusion protein between the gpD protein and the nuclear localization signal sequence expressed by the vector and, a λ phage having the nuclear localization signal attached to its head was obtained. That is, we have found that the fusion protein expressed in *E. coli* has been complementarily integrated into the phage head which does not express the protein.

Next, we have obtained a similar result by introducing the vector that expresses the fusion protein between the gpD protein and the nuclear localization shignal sequence into the *E. coli* lysogenized by the mutant λ phage, and by heat-inducing the lysogenic phage. More specifically, we introduced the vector that expresses the above fusion protein into the *E. coli* lysogenized by the D amber phage, and heat-induced the transformants. As the result, the phage whose head has not incorporated the fusion protein and consists of the gpE protein became sensitive to EDTA, while the phage which has incorporated the fusion protein exhibited resistance to EDTA. Next, we treated the resulting phage with EDTA and measured the titer. As a result, it was revealed that the phage packaged with 80% genome size DNA was constructed, and that the fusion protein was incorporated in the phage head. In addition, we have confirmed that the phage had the nuclear localization signal exposed on the outer surface of the head. We also confirmed that the phage incorporating the fusion protein was formed in the same manner even when we used 100% genome size DNA. Furthermore, we introduced the phage having the nuclear localization signal exposed on the outer surface of its head into HEL-R66 cells, which are human fetal lung cells, by microinjection and proved that the phage has a nuclear translocation activity, thereby completing the present invention.

Therefore, the present invention relates to a λ phage capable of packaging macromolecules such as long chain DNA and having a nuclear translocation activity.

More specifically, it relates to:

(1) a phage or its head having a protein containing a nuclear localization signal as a component of the head, (2) the phage or its head of (1), wherein said nuclear localization signal comprises any one of the sequences described in SEQ ID NO: 1 to SEQ ID NO: 4.

(3) the phage or its head of (1), wherein said phage is a λ phage, (4) the phage or its head of (3), wherein said protein containing the nuclear localization signal is a fusion protein between the nuclear localization signal and a phage head protein, (5) the phage or its head of (4), wherein said phage head protein is D protein of a λ phage, (6) a fusion protein between a nuclear localization signal and a protein that forms a phage head, (7) the fusion protein of (6), wherein said nuclear localization signal comprises any one of the sequences described in SEQ ID NO: 1 to SEQ ID NO: 4.

(8) the fusion protein of (6), wherein said phage is a λ phage, (9) the fusion protein of (6), wherein said phage head protein is the D protein of a λ phage,

(10) a DNA encoding any one of the proteins of (6) to (9),

(11) a vector containing the DNA of (10),

(12) a bacterial host carrying the vector of (11),

(13) the bacterial host of (12), wherein said host is *Escherichia coli*,

(14) a kit for transforming cells, wherein said kit comprises the bacterial host of (12) or (13), and (b) a phage from which a head protein contained in a fusion protein expressed in said host has been derived, wherein said phage cannot express said head protein in said bacterial host,

(15) the kit of (14), wherein said phage is a λ phage,

(16) the kit of (14), wherein said head protein contained in the fusion protein expressed in the bacterial host is D protein of a λ phage,

(17) a method fortranslocating a desired substance into the nucleus of a desired cell, wherein said method comprises: (a) packaging into the phage or into its head of (1) the desired substance to be translocated to the nucleus, and (b) introducing said phage or its head into the desired cell,

(18) the method of (17), wherein said desired substance is a nucleic acid,

(19) the method of (17), wherein said phage is a λ phage,

(20) the method of (17), wherein said cell is a mammalian cell.

The present invention relates to the technology to package an exogenous material into the head of a phage to which a nuclear localization signal is attached, introduce the phage into a desired cell in which the exogenous material is to function, and translocate the exogenous material together with the phage particle into the nucleus of the target cell.

The nuclear localization signal used in the present invention is not particularly limited as far as it has the activity to translocate a substance to which the signal sequence is attached into the nucleus. For example, in the case of translocating the λ phage particle into the nucleus, it is preferable to use the nuclear localization signal of SV40 VP1, SV40 large T antigen, or hepatitis D virus δ antigen, or a sequence containing "PKKKRKV (SEQ ID NO: 4) (by the single letter representation of amino acids as is found in Encyclopedia of Biochemistry, 2nd ed.)" that is the minimum unit having the nuclear translocation activity within the nuclear localization signal of SV40 large T antigen.

The phage used in the present invention is not particularly limited as far as an exogenous material can be packaged into its head. Phages such as a λ phage and an M13 phage can be used.

A number of methods can be used to prepare the phage whose head is constituted by a protein containing the nuclear localization signal. For example, one can chemically bind the nuclear localization signal sequence to a phage head protein, or combine a DNA encoding the nuclear localization signal sequence with gene encoding a phage head protein and incorporate it into a vector, express it as a fusion protein a bacterial host, and proliferate in the host a mutant phage that cannot express the head protein, thereby constructing the phage head. There are no limitation to the vectors that can be used in the above methods, and various vectors can be used. The bacterial host is not particularly limited as far as the phage used in the method can proliferate in the host. For example, when a λ phage is used, a variety of *E. coli* strains in which the phage can proliferate can be used. The nuclear localization signal sequence may chemically bind to the phage head protein, directly or via a cross-linking agent or a spacer peptide. The DNA encoding the nuclear localization signal sequence and the gene encoding a phage head protein may be combined directly or through a spacer nucleotide.

The head protein used in the above methods non-limitedly include gpD protein or gpE protein when the phage is a λ phage, and gene 3 protein when the phage is M13.

In the present invention, the phage is introduced into the cell after packaging an exogenous material. As for packaging, the method of Ishiura et al. (Gene 82: 281–289 (1989)) or the method of Sternberg et al. (Japanese Patent No. Hei 59-500042) can be used. As for the exogenous material, a gene, a gene fragment, ribozyme, an antisense gene, or any other substance to make it function in the nucleus can be used. For example, when gene therapy is performed, it will be effective to use the normal counterpart of a defective gene. When the function of a specific gene is analyzed, it will be effective to use an antisense gene against the gene. Also, if one wishes to create transgenic animals, it will be effective to introduce a gene which is associated with the phenotype to be conferred into them. It should be noted that the present invention enables packaging a long chain nucleic acid such as a gene with its upstream region.

The method to introduce the phage that has packaged an exogenous material, includes the microinjection method, the lipofection method, the liposome method, the HVJ-liposome method, the immuno-liposome method, the pH-sensitive liposome method, the erythrocyte ghost method, the DEAE-dextran method, the method utilizing endocytosis of a receptor on the cell surface, the method utilizing a specific antigen on the cell surface, the method utilizing a synthetic macromolecular carrier, the method utilizing a particle gun, etc. There is no particular limitation to the cells into which the phage packaging an exogenous material is introduced, and various cells can be used depending on the purposes.

BEST MODE FOR IMPLEMENTING THE INVENTION

The present invention is described in more detail with reference to the following examples, but is not construed to be limited thereto.

EXAMPLE 1

Construction of a λ Phage With a Nuclear Localization Signal

Using a wild type λ phage gene as a template, cDNA for the gpD protein, which is one of the proteins to constitute the λ phage head, was cloned by PCR. The PCR was done according to the method of Sternberg et al. (Sternberg et al., PNAS 92: 1609–1613 (1995)). More specifically, 5'-GTAAGCCATGGTTATGACGAGCAAAG-3' (which contains an NcoI site at the 6th to 11th nucleotide residues from the 5' side) (SEQ ID NO: 5) and 5'-GTTCGAATTCCTATTAAACGATGCTGATTGCC-3' (which contains an EcoRI site at the 5th to 10th nucleotide residues from the 5' side) (SEQ ID NO: 6) were used as primers, and a fragment of about 4 kb containing the gpD gene, which was generated by digesting 20 μg of the λ phage genome (TOYOBO, 7.9 OD/ml) with ApaI and ApaLI, was used as a template. The PCR reaction was done using 0.2 μg of the template, 10×Reaction buffer (Pharmacia; 500 mM KCl, 15 mM $MgCl_2$, 100 mM Tris-HCl (pH 9.0)), 1 μM each of primers, 50 μM dNTP, 100 μl of 5 U Taq DNA polymerase (Pharmacia) by performing 25 cycles of the steps containing heat denaturation at 90° C. for 3 min, annealing at 55° C. for 2 min, and extension at 72° C. for 3 min and finally one cycle of heat denaturation at 90° C. for 3 min, annealing at 55° C. for 2 min, and extension at 72° C. for 10 min. The DNA fragment amplified by the above PCR was introduced into the NcoI and EcoRI sites of an E. coli expression vector, pTrcHisA (Invitrogen). The resulting vector was designated "pTrcHisA-gpD." After confirming the DNA sequence by the cycle sequencing method, the vector was introduced into E. coli TOP10 (Seth G. N. Grant et al., PNAS 87: 4645–4649 (1990)), and the gpD protein was expressed at a high level in the E. coli. The expression of the protein was examined by SDS polyacrylamide gel electrophoresis (SDS-PAGE). As a result, a strong band was detected at the 11.6 kDa position, which is the molecular weight of the protein, 6 hrs after the induction by 1 mM IPTG.

Next, E. coli TOP10 (pTrcHisA-gpD) and E. coli 594 (pTrcHisA-gpD), which are expressing the gpD protein because "pTrcHisA-gpD" has been introduced and which does not contain a suppressor mutation ($sup^0$), were infected with the D amber phage, and the plaque forming activity and the titer were examined. The results indicated that plaques were formed in both cases and that the titers were equivalent to the one with LE392, which contains a suppressor mutation against D amber. Therefore, it was demonstrated that the phage is formed by functional complementation even when the gpD gene exists in trans.

Figure 1:
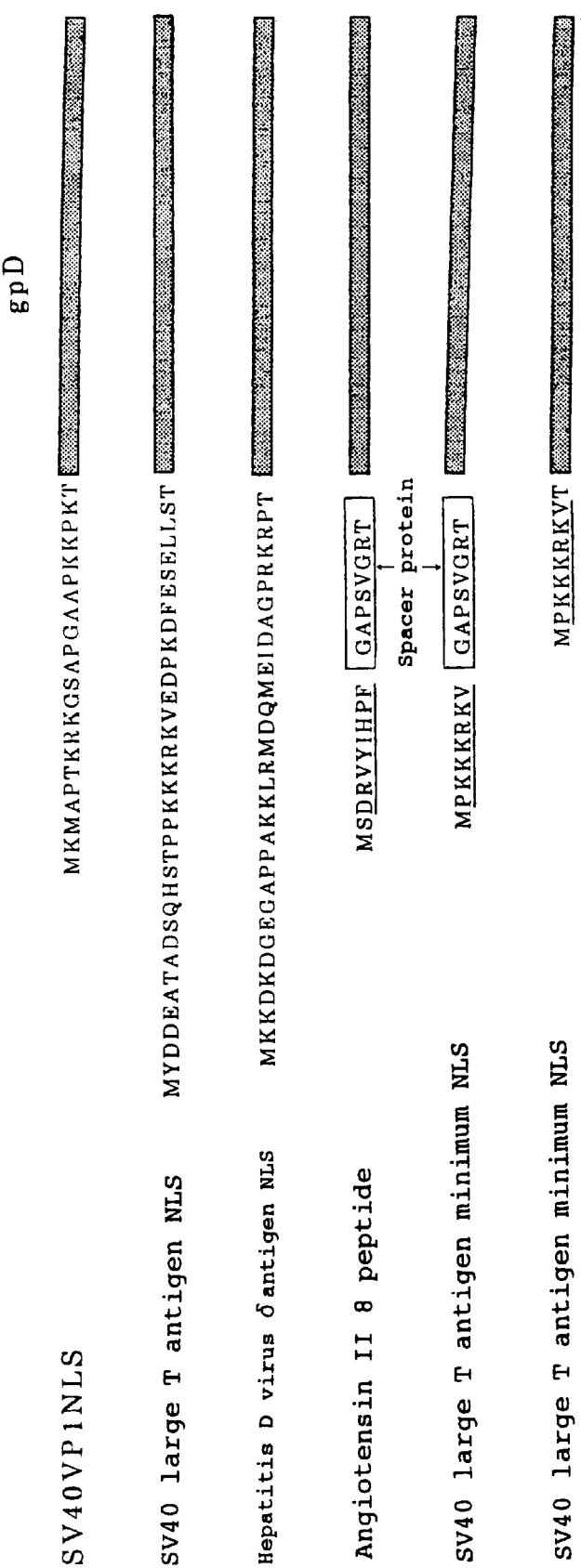
FIG. 1 shows a diagram of fusion proteins between various nuclear localization signals and the gpD protein, which is a λ phage head protein. Depicted sequences are as follows, SV40VP1NLS (SEQ ID NO:7), SV40 large T antigen NLS (SEQ ID NO:8), Hepatitis D virus δ antigen NLS (SEQ ID NO:9), angiotensin II 8 peptide (SEQ ID NO:10), Sv40 large T antigen minimum NLS (spacer protein) (SEQ ID NO:11), SV40 large T antigen minimum NLS (SEQ ID NO:12).
Figure 2A:
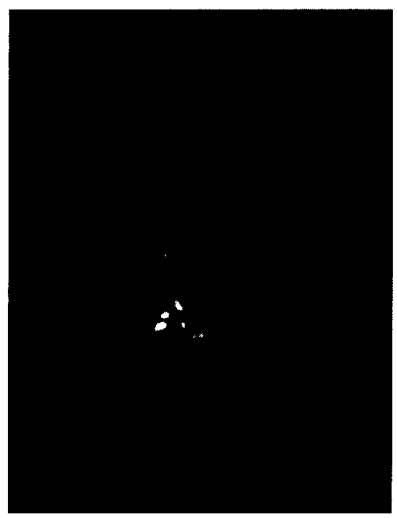
FIG. 2 shows microscopic photographs indicating the nuclear translocation activity of the λ phage to which a nuclear localization signal was attached via a cross-linking agent.
Figure 2B:
Figure 2C:
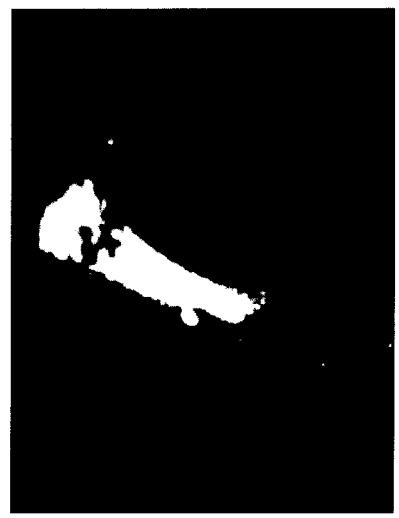
Figure 2D:

Then, the phage with a nuclear localization signal was constructed by expressing a fusion protein between a nuclear localization signal and gpD in E. coli. As the nuclear localization signal, in addition to the three types of nuclear localization signal from SV40VP1, SV40 large T antigen, and hepatitis D virus δ antigen (SEQ ID NOS: 1, 2, and 3 respectively), all of which were confirmed to be effective by the present inventors, two other types of nuclear localization signal, which were (1) a fusion protein between the minimum unit of the nuclear localization signal "PKKKRKV (SEQ ID NO: 4)" and a spacer protein, and (2) the minimum unit of the nuclear localization signal "PKKKRKV" (SEQ ID NO: 4) alone, were used. Also, a fusion protein between an 8 polypeptide from angiotensin II (which is not a nuclear localization signal) described in Sternberg et al., PNAS 92: 1609–1613 (1995) and a spacer protein was used in order to confirm the phage formation capability, making the total of six types (FIG. 1). Next, the oligonucleotides corresponding to these nuclear localization signals were synthesized, and introduced into the NcoI site of the above-described "pTrcHisA-gpD". After confirming that the plasmids were correctly constructed by cycle sequencing method, the vectors were introduced into E. coli Top10, and the fusion proteins between the nuclear localization signals and the gpD protein were expressed at a high level in the E. coli. The expression of the fusion proteins was examined by SDS polyacrylamide gel electrophoresis (SDS-PAGE). As a result, a strong band was detected at the expected position for the molecular weight of the desired protein 6 hrs after the induction by 1 mM IPTG. Further, the plaque formation capability was examined by infecting the bacterial cells with the D amber phage, and plaque formation was observed when three types of peptides, SV40 large T antigen, hepatitis D virus δ antigen, and a fusion protein between the 8 polypeptide from angiotensin II and a spacer protein, were used. The titer measurements indicated that all the phage had a titer on the order of $10^{10}$, but that the plaque forming time was 10 hrs for SV40 large T antigen, and 18 hrs for hepatitis D virus δ antigen, showing delays compared with the 6 hrs which is normal plaque forming time (Table 1).

TABLE 1

| Host E. coli strain | Titer (PFU/ml) | Plaque forming time |
|---|---|---|
| LE392 (supE44, supF58) | $1.8 \times 10^{10}$ | 6 hrs |
| TOP10 (sup$^0$)/ pTrc-gpD (no induction) | $0.5 \times 10^{10}$ | 6 hrs |
| TOP10 (sup$^0$)/ pTrc-angiotensin II-gpD (IPTG induction) | $0.6 \times 10^{10}$ | 6 hrs |
| TOP10 (sup$^0$)/ pTrc-SV40 large T antigen-gpD (IPTG induction) | $0.4 \times 10^{10}$ | 10 hrs |
| TOP10 (sup$^0$)/ pTrc-hepatitis D virus δ antigen-gpD (IPTG induction) | $0.2 \times 10^{10}$ | 18 hrs |

It was also confirmed that the phage particle thus obtained contain the fusion proteins between the nuclear localization signals and gpD by the western blotting method.

EXAMPLE 2

Packaging of the λ Phage Genome by the λ Phage With a Nuclear Localization Signal In place of the above method in which the phage was formed by the infection of E. coli TOP10, the method expected to provide better phage formation capabilities in which a lysogenic phage (E. coli 594) or an 80% genome phage is heat-induced were used in the following. E. coli 594 (λ Dam15 cIts857 Sam7) is lysogenized by a 100% genome phage, and has a temperature sensitive repressor cI which is inactivated by the treatment at 42° C. for 15 min. Because of the D amber mutation, however, the head cannot be produced and only the tail is produced in this sup$^0$ strain of E. coli. "pTrcHisA-gpD" was introduced into this E. coli strain to allow the expression of the fusion proteins, and the phage formation was examined by heat induction. As a result, the phage was formed when any one of the six types of peptides as described above was used. The results indicated that the fusion proteins were incorporated into the head of the phage in this E. coli strain lysogenized by a 100% genome phage. The titers of the resulting phage are shown in Table 2.

TABLE 2

| Proteins expressed | Titer (PFU/ml) (analyzed with E. coli LE392) |
|---|---|
| — | 0 |
| gpD | $5 \times 10^8$ |
| SV40 large T antigen-gpD fusion protein | $3.6 \times 10^8$ |
| SV40VP1-gpD fusion protein | $3.0 \times 10^8$ |
| hepatitis D virus δ antigen-gpD fusion protein | $3.3 \times 10^8$ |
| angiotensin II-spacer-gpD fusion protein | $5 \times 10^8$ |
| PKKKRKV-spacer-gpD fusion protein | $1.7 \times 10^8$ |
| PKKKRKV-gpD fusion protein | $8.9 \times 10^7$ |

Next, another set of experiments were performed using E. coli 594 lysogenized by an 80% genome D amber phage. cI, which is the repressor of the phage and encoded by the phage, is temperature sensitive, and becomes inactive by a treatment at 42° C. for 15 min, which results in lysis of the bacteria by the phage. In addition, since the phage contains the D amber mutation, it cannot express gpD in this sup$^0$ host, and the head is usually formed only with gpE. (There are two kinds of λ phage head proteins-gpD and gpE.) The phage having only gpE is extremely sensitive to EDTA. On the other hand, if the E. coli is allowed to express the fusion protein and the heat-induced phage incorporates the fusion protein, it would show EDTA resistance. "pTrcHisA-gpD" was introduced into the E. coli strain, then the phage was prepared on the 8 ml scale, and treated with 10 mM EDTA. E. coli LE392 was infected with them to measure their titers. As a result, the EDTA resistance was confirmed using any one of the six types of peptides used in Example 1. The results indicated that the 80% genome phage have higher titers than the 100% genome phage, suggesting that the head structure is stabilized in the former (Table 3).

TABLE 3

| | Titer (PFU/ml) (analyzed with E. coli LE392) | |
|---|---|---|
| Proteins expressed | EDTA (−) | EDTA (+) |
| — | $4.0 \times 10^9$ | 0 |
| gpD | $8.6 \times 10^8$ | $6.8 \times 10^8$ |
| SV40 large T antigen-gpD fusion protein | $9.8 \times 10^9$ | $8.0 \times 10^9$ |
| SV40VP1-gpD fusion protein | $2.3 \times 10^8$ | $2.4 \times 10^8$ |
| hepatitis D virus δ antigen-gpD fusion protein | $5.6 \times 10^8$ | $5.6 \times 10^8$ |
| angiotensin II-spacer-gpD fusion protein | $7.1 \times 10^8$ | $8.4 \times 10^8$ |
| PKKKRKV-spacer-gpD fusion protein | $2.3 \times 10^8$ | $2.3 \times 10^8$ |
| PKKKRKV-gpD fusion protein | $1.8 \times 10^8$ | $1.5 \times 10^8$ |

EXAMPLE 3

Nuclear Translocation Activities of the λ Phage to Which the Nuclear Localization Signal is Attached Through a Cross-Linking Agent (1) Preparation of Phage Particles From λ Phage Lysogenic Bacteria E. coli w3350thy$^-$ (λ cI847 Sam7) lysogenized by λ phage was cultured in the LB (thy) medium at 32° C., and at the logarithmic growth phase ($2\times10^8$ cells/ml) it was shaken at 45° C. for 25 min to induce the phage production. Then, the culture was shaken at 39° C. for 3 hrs, centrifuged at 5,000 rpm for 10 min, and the precipitated E. coli was resuspended in the SM buffer (0.1 M NaCl, 8 mMMgSO$_4$, 0.01% gelatin, 50 mM Tris-HCl (pH 7.5)). The concentrated bacteria were lysed by adding 37° C. chloroform and stirring. Further, the solution was added with DNase, centrifuged at 8,000 rpm for 30 min to remove insoluble matters, and the supernatant was centrifuged at 23,000 rpm for 60 min to precipitate the phage, and the phage were resuspended in the SM buffer. The recovered phage particles were purified by cesium chloride density-gradient centrifugation.

(2) Cross-Linking the Nuclear Localization Signal to the λ Phage

A cross-linking agent (SMPB; Pierce) was used to cross-link the nuclear localization signal to the λ phage. SV40 large T antigen (SEQ ID NO: 2) was used as the nuclear localization signal. The λ phage was prepared at 1.1 mg/ml in a buffer (0.1 M NaCl, 8 mM MgSO$_4$, 20 mM Hepes.NaOH (pH 7.0)). 10 mM SMPB dissolved in anhydrous DMSO was added at a 5,000 times molar ratio to the phage particles, and the mixture was incubated at 25° C. for 1 hr. The mixture was then dialyzed against a buffer (0.1 M NaCl, 8 mM MgSO$_4$, 20 mM Tris-HCl (pH 7.5)) overnight and the SMPB-modified λ phage was obtained by removing the unreacted SMPB. The synthetic nuclear localization signal peptide (Sawady Technology) was dissolved at equimolar with SMPB in 20 mM Tris-HCl (pH 8.0) containing 0.1M NaCl, and DTT was added to 50 mM to the solution, and reduction reaction was carried out at 37° C. for 1 hr. After removing DTT by gel filtration in a buffer (0.1M NaCl, 8 mM $MgSO_4$, 20 mM Hepes.NaOH (pH 7.0)), the eluate was added to the SMPB-modified phage, and allowed to react at 25° C. for 3 hrs. The reaction solution was put into a centrifuge tube so as to layer over a layer of 1 ml of 10% sucrose solution (containing 0.1M NaCl, 8 mM $MgSO_4$, 20 mM Hepes-NaOH (pH 7.0)) previously placed in the tube, centrifuged at 4° C. at 20,000 rpm (Beckman TLS-55 rotor) for 1 hr. The precipitate was resuspended in a buffer (0.1M NaCl, 8 mM $MgSO_4$, 20 mM Hepes.NaOH (pH 7.0)) to recover the phage to which the nuclear localization signal was attached.

(3) Detection of the Nuclear Translocation Activity by Microinjection and the Indirect Fluorescent Antibody Method The λ phage with the nuclear localization signal was microinjected into the cytoplasm of the cells cultured on a cover slip by the method described in the literature (Y. Yoneda et al., Exp. Cell. Res. 170: 439–452 (1987), T. Tachibana et al., J. Biol. Chem. 269: 24542–24545 (1994)). After the cells were incubated at 37° C. for 5 min to 4 hrs, PBS (−) containing 3.7% formaldehyde was added to fix the cells at room temperature for 20 min. The range of incubation time "5 min to 4 hrs" before the fixation was set in order to measure the time necessary for the λ phage with the nuclear localization signal to reach the nucleus after the injection. The cells were treated with 0.5% Triton X-100 for 5 min at room temperature after the fixation, and immersed in 10% Block Ace (Dainippon Pharmaceutical) for 1 hr at room temperature for blocking. Next, the cells were reacted at room temperature for 1 hr with a 500-fold dilution of the rabbit anti-λ phage serum (obtained from Dr. Hideyuki Ogawa, Osaka University) as the primary antibody, then reacted at room temperature for 1 hr with the FITC-labeled anti-rabbit IgG (6 μg/ml) as the secondary antibody, the localization of the λ phage with the nuclear localization signal in the cell was examined using a fluorescent microscope. The results confirmed that the λ phage with the nuclear localization signal translocates to the nucleus immediately after the microinjection (FIG. 2, upper left), and remains in the periphery of the nucleus at 30 min after microinjection (FIG. 2, upper right). The unmodified λ phage used as a control in this experiment, which does not have a nuclear localization signal, dispersed in the cytoplasm immediately after the microinjection (FIG. 2, lower left), and diffused almost homogeneously within 30 min (FIG. 2, lower right).

EXAMPLE 4

Analysis of Surface Exposure of the Nuclear Localization Signal on the Phage Head A cysteine residue at the N-terminal side of the synthetic Sv40 large T antigen was cross-linked with SulfoLink Gel (Pierce) to prepare an immobilized column (2 ml, 5 cm). Ten ml of anti-SV40LT rabbit serum was treated with saturated ammonium sulfate, and equilibrated by dialysis over the coupling buffer (50 mM Tris-HCl (pH 8.5), 5 mM EDTA-Na). This was applied onto the column, and the binding antibody was eluted in 0.1M Gly-HCl (pH 2.5) fractionated in 0.5 ml portions, and the eluted fraction was neutralized by 0.5 ml of 2M Tris-HCl (pH 8.0). Ten mg of the affinity-purified antibody thus obtained was reacted with $3 \times 10^8$ molecules of the 80% genome phage expressing SV40 large T antigen (hereinafter designated as "LT-phage") at 4° C. overnight. One hundred ml of Protein A-Sepharose 4B (Pharmacia, 50% slurry) was added thereto, allowed to react at room temperature for 1 hr for absorption, centrifuged at 5,000 rpm for 5 min, and the titer of the non-absorbed phage in the supernatant was measured using E. coli LE392. As a control, the phage expressing only the gpD protein was similarly analyzed. In addition, similar analyses were made using the rabbit γ globulin in place of the anti-SV40LT rabbit serum, and also without using these antibodies (Table 4).

TABLE 4

| | Titer (PFU/ml) (analyzed with E. coli LE392) | | | | | |
|---|---|---|---|---|---|---|
| | Anti-SV40 large T antigen Nuclear localization signal antibody | | Rabbit γ globulin | | No antibody | |
| Protein expressed | pre-RXN | post-RXN | pre-RXN | post-RXN | pre-RXN | post-RXN |
| D | $3 \times 10^8$ | $2.7 \times 10^8$ | $3 \times 10^8$ | $3.0 \times 10^8$ | $3 \times 10^8$ | $3.0 \times 10^8$ |
| SV40 large T antigen-gpD fusion protein | $3 \times 10^8$ | $2.4 \times 10^7$ | $3 \times 10^8$ | $2.4 \times 10^8$ | $3 \times 10^8$ | $2 \times 10^8$ |

The results indicated that most of the "LT-phage" had the NLS exposed on the surface of the head, as evidenced by an approximately 1/10 reduction in the titer (from $3 \times 10^8$ to $2.4 \times 10^7$).

EXAMPLE 5

Nuclear Translocation Activities of the λ Phage Having Nuclear Localization Signals Exposed on the Head Surface The plasmid which can express the fusion protein between SV40 large T antigen and gpD was introduced into the E. coli TOP10 lysogenized by the 80% genome D amber phage. The bacteria were cultured in the LB (10 mM $MgSO_4$, 100 μg/ml ampicillin) medium at 32° C., and at the logarithmic growth phase ($2 \times 10^8$ cells/ml) the culture was shaken at 45° C. for 20 min to induce the phage production. Then the culture was shaken in the presence of 1 mM IPTG for 3 hrs at 39° C., centrifuged at 5,000 rpm for 10 min, and the precipitated E. coli cells were resuspended in the A-buffer (10 mM Tris-HCl (pH 7.5), 10 mM $MgSO_4$, 0.01% gelatin, 10 mM putrescine). The concentrated bacteria were lysed at 37° C. by adding chloroform and stirring. Further, the solution was added with DNase, and centrifuged at 8,000 rpm for 30 min to remove insoluble matters. The supernatant was added with 10% polyethylene glycol #6000 and 1M NaCl, treated at 0° C. for 2 hrs, and centrifuged at 8,000 rpm for 30 min to precipitate the phage. The phage was resuspended in the λ-buffer and the recovered phage particles were purified by cesium chloride density-gradient ultracentrifugation.

Figure 3A:
FIG. 3 shows microscopic photographs indicating the nuclear translocation activity of the λ phage having a nuclear localization signal exposed on the surface of its head.
Figure 3B:
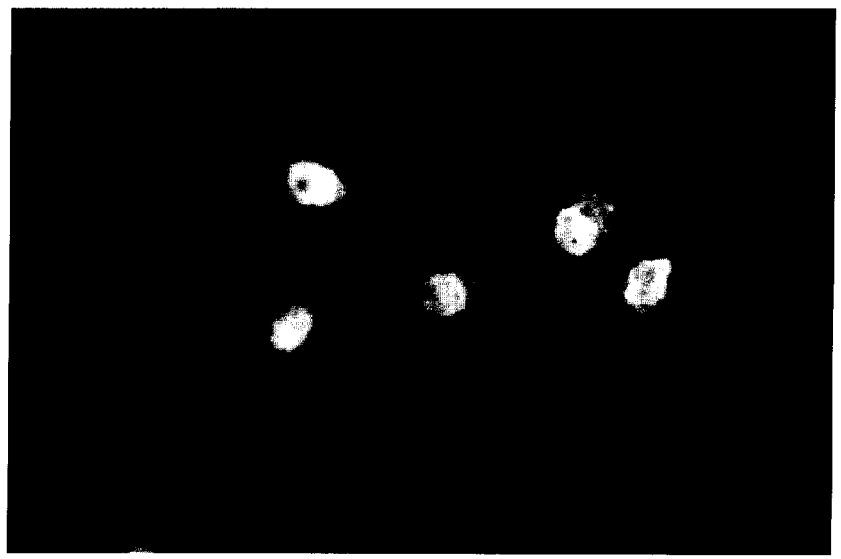

The phage particles were dissolved in the λ-buffer to 2 mg/ml, and microinjection was carried out in the same manner as in Example 3 (3). The serum prepared by sensitizing the rabbit with the wild type λ phage together with Freund's adjuvant was used as the primary antibody for detection. The results confirmed that while the wild type λ phage, used as a control, did not exhibit the nuclear translocation activity (FIG. 3, top), the λ phage with the nuclear localization signal had accumulated in the nucleus in 30 min (FIG. 3, bottom).

INDUSTRIAL APPLICABILITY

The present invention provides the λ phage with the nuclear localization signal capable of packaging macromolecules such as long chain DNA and having a nuclear translocation activity. This phage can, for example, transport desired foreign genes, as long chain DNAs including the upstream regions, to the nucleus, and therefore it is expected to be utilized effectively in a variety of fields such as clarification of biological phenomena and gene therapy.

What is claimed is:

1. A phage or its head comprising a nuclear localization signal as a component of the head, wherein said nuclear localization signal is exposed on the outer surface of the phage head and wherein said nuclear localization signal comprises any one of the sequences described in SEQ ID NO: 1 to SEQ ID NO: 3.

2. A phage or its head comprising a nuclear localization signal as a component of the head, wherein said nuclear localization signal is exposed on the outer surface of the phage head and wherein said phage is a λ phage.

3. The phage or its head of claim 2, wherein said nuclear localization signal is comprised within a fusion protein between said nuclear localization signal and a phage protein.

4. The phage or its head of claim 3, wherein the phage head protein is the D protein of λ phage.

5. The phage or its head of claim 3, wherein said fusion protein is encoded by a nucleic acid.

6. A phage or its head comprising a nuclear localization signal as a component of the head, wherein said nuclear localization signal is exposed on the outer surface of the phage head and wherein said nuclear localization signal is chemically cross-linked to the phage head.

* * * * *

UNITED STATES PATENT AND TRADEMARK OFFICE
CERTIFICATE OF CORRECTION

PATENT NO. : 6,235,521 B1
DATED : May 22, 2001
INVENTOR(S) : Mahito Nakanishi et al.

It is certified that error appears in the above-identified patent and that said Letters Patent is hereby corrected as shown below:

Title page, Item [54] and Column 1, lines 1 and 2,
Title, replace "PHAGE BONDED TO A NUCLEAR LOCATION SIGNAL" with -- PHAGE WITH NUCLEAR LOCALIZATION SIGNAL --;

Title page,
Item [73], Assignee, replace "Dnavec Research" with -- Dnavec Research Inc. --;

Column 1,
Line 16, replace "avirus" with -- a virus --;
Lines 32 and 33, replace "have currently being developed" with -- are currently being developed --;
Line 41, replace "phosphate.," with -- phosphate, --;

Column 3,
Line 1, replace "shignal" with -- signal --;

Column 4,
Line 1, replace "fortranslocating" with -- for translocating --;
Line 43, replace "limitation" with -- limitations --;

Column 5,
Line 30, after "Fig.2" insert -- (Panels A-D) --;

Column 8,
Line 46, replace "8 mMMgS0$_4$" with -- 8 mM MgSO$_4$ --;
Lines 61-62, replace "Hepe-s.NaOH" with -- Hepes•NaOH --;

Column 9,
Lines 7, and 14, replace "Hepes.NaOH" with -- Hepes•NaOH --;
Line 11, replace "Hepes-NaOH" with -- Hepes•NaOH --.

UNITED STATES PATENT AND TRADEMARK OFFICE
CERTIFICATE OF CORRECTION

PATENT NO.    : 6,235,521 B1
DATED         : May 22, 2001
INVENTOR(S)   : Mahito Nakanishi et al.

It is certified that error appears in the above-identified patent and that said Letters Patent is hereby corrected as shown below:

Column 10,
Line 7, replace "Sv40" with -- SV40 --;
Line 48, replace "2.4X10$^7$" with --2.4X10$^8$ --; and
Line 65, replace "A-buffer" with -- λ-buffer --.

Signed and Sealed this

Twentieth Day of April, 2004

JON W. DUDAS
*Acting Director of the United States Patent and Trademark Office*